US010943677B2

(12) United States Patent
Reicher et al.

(10) Patent No.: US 10,943,677 B2
(45) Date of Patent: Mar. 9, 2021

(54) REPORT LINKS

(71) Applicant: MERGE HEALTHCARE SOLUTIONS INC., Hartland, WI (US)

(72) Inventors: Murray A. Reicher, Rancho Santa Fe, CA (US); Evan K. Fram, Paradise Valley, AZ (US)

(73) Assignee: MERGE HEALTHCARE SOLUTIONS INC., Hartland, WI (US)

( * ) Notice: Subject to any disclaimer, the term of this patent is extended or adjusted under 35 U.S.C. 154(b) by 1156 days.

(21) Appl. No.: 15/195,552

(22) Filed: Jun. 28, 2016

(65) Prior Publication Data

US 2017/0039349 A1 Feb. 9, 2017

Related U.S. Application Data

(62) Division of application No. 14/017,148, filed on Sep. 3, 2013, now Pat. No. 10,181,360.
(Continued)

(51) Int. Cl.
*G06Q 10/00* (2012.01)
*G06F 15/16* (2006.01)
(Continued)

(52) U.S. Cl.
CPC ......... *G16H 10/60* (2018.01); *G06Q 10/1095* (2013.01); *G16H 15/00* (2018.01); *H04L 67/22* (2013.01); *H04L 67/02* (2013.01)

(58) Field of Classification Search
CPC ........... A61N 1/08; G06F 17/30; G06F 19/30; G06F 19/32; G06F 19/325; G06F 19/326;
(Continued)

(56) References Cited

U.S. PATENT DOCUMENTS 5,664,109 A * 9/1997 Johnson ................. G06Q 40/08
705/2
2007/0214002 A1 9/2007 Smith et al.
(Continued)

OTHER PUBLICATIONS

AGFA HealthCare, color brochure "IMPAX 6: Digital Image and Information Management," © 2012 Agfa HealthCare N.V. Downloaded from http://www.agfahealthcare.com/global/en/he/library/libraryopen?ID=32882925. Accessed on Feb. 9, 2015.
(Continued)

*Primary Examiner* — Maroun P Kanaan
(74) *Attorney, Agent, or Firm* — Michael Best & Friedrich LLP

(57) ABSTRACT

A medical and/or clinical report includes one or more links to various external (and/or internal) data sources and/or systems that include information relevant to the medical report. In an embodiment, a medical report may be in a PDF format and include links to images associated with the exam, information regarding the patient, a scheduling application useful to schedule additional procedures for the patient, and/or any other information associated with the patient or exam. The medical report, including various links, may be generated based on information received from external medical data systems. For example, a medical report from an external system may be updated to include various links to systems and sources of data related to the medical report, as described herein.

18 Claims, 12 Drawing Sheets

Related U.S. Application Data

(60) Provisional application No. 61/696,763, filed on Sep. 4, 2012, provisional application No. 61/709,626, filed on Oct. 4, 2012.

(51) Int. Cl.
| | |
|---|---|
| *G06Q 50/00* | (2012.01) |
| *G16H 10/60* | (2018.01) |
| *G06Q 10/10* | (2012.01) |
| *G16H 15/00* | (2018.01) |
| *H04L 29/08* | (2006.01) |

(58) Field of Classification Search
CPC .. G06F 19/34; G06F 19/3418; G06F 19/3456; G06F 19/3468; G06F 19/3475; G06F 19/3481; G06F 19/36; G06F 21/6218; G06F 19/321; G06F 19/3462; G06F 21/6227; G06F 21/31; G06F 19/328; G06F 21/6245; G06F 21/60; G06F 19/324; G06F 19/00; G06F 6/2455; G06Q 10/10; G06Q 40/08; G06Q 50/22; G06Q 50/24; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 30/20; G16H 30/40; G16H 40/00; G16H 40/20; G16H 40/40; G16H 40/60; G16H 40/63; G16H 40/67; G16H 50/00; G16H 50/20; G16H 50/30; G16H 50/50; G16H 50/70; G16H 5/80; G16H 70/00; G16H 70/20; G16H 70/14; G16H 70/60; G16H 80/00

See application file for complete search history.

(56) References Cited

U.S. PATENT DOCUMENTS

| | | | | |
|---|---|---|---|---|
| 2009/0012816 | A1 | 1/2009 | Cookcon et al. | |
| 2010/0088121 | A1* | 4/2010 | Shih | G16H 80/00 705/3 |
| 2010/0299157 | A1 | 11/2010 | Fram et al. | |
| 2010/0305970 | A1* | 12/2010 | McLaren | G06F 19/00 705/3 |
| 2011/0015941 | A1* | 1/2011 | Backhaus | G16H 30/40 705/2 |
| 2011/0110568 | A1* | 5/2011 | Vesper | G06F 19/321 382/128 |

OTHER PUBLICATIONS

AGFA HealthCare, IMPAX 6.5 Datasheet (US)2012. © 2012 Agfa HealthCare N.V. Downloaded from http://www.agfahealthcare.com/global/en/he/library/libraryopen?ID=37459801. Accessed on Feb. 9, 2015.
AMD Technologies, Inc., Catella PACS 5.0 Viewer User Manual (112 pgs), © 2010, AMD Technologies, Inc. (Doc. 340-3-503 Rev. 01). Downloaded from http://www.amdtechnologies.com/lit/cat5viewer.pdf. Accessed on Feb. 9, 2015.
ASPYRA's Imaging Solutions, 3 page color print out. Accessed at http://www.aspyra.com/imaging-solutions. Accessed on Feb. 9, 2015.
AVREO, interWorks—RIS/PACS package, 2 page color brochure, © 2014, Avreo, Inc. (Document MR-5032 Rev. 4). Downloaded from http://www.avreo.com/ProductBrochures/MR-5032Rev.%204interWORKS%20RISPACSPackage.pdf. Accessed on Feb. 9, 2015.
BRIT Systems, BRIT PACS View Viewer, 2 page color brochure, (BPB-BPV-0001). Downloaded from http://www.brit.com/pdfs/britpacsview.pdf. Accessed on Feb. 9, 2015.
BRIT Systems, Roentgen Works—100% Browers-based VNA (Vendor Neutral Archive/PACS), © 2010 BRIT Systems, 1 page color sheet. Accessed at http://www.roentgenworks.com/PACS. Accessed on Feb. 9, 2015.
BRIT Systems, Vision Multi-modality Viewer—with 3D, 2 page color brochure, (BPB-BVV-0001 REVC). Downloaded from http://www.brit.com/pdfs/BPB-BVV-0001REVO_BRIT_Vision_Viewer.pdf. Accessed on Feb. 9, 2015.
CANDELiS, ImageGrid™: Image Management Appliance, 6 page color brochure. (AD-012 Rev. F Nov. 2012), © 2012 Candelis, Inc. Downloaded from http://www.candelis.com/images/pdf/Candelis_ImageGrid_Appliance_20111121.pdf. Accessed on Feb. 9, 2015.
Carestream, Cardiology PACS, 8 page color brochure. (CAT 866 6075 06/12). © Carestream Health, Inc., 2012. Downloaded from http://www carestream.com/cardioPACS_brochure_M1-877.pdf. Accessed on Feb. 9, 2015.
Carestream, Vue PACS, 8 page color brochure. (CAT 300 1035 05/14). © Carestream Health, Inc., 2014. Downloaded from http://www.carestream.com/csPACS_brochure M1-876.pdf. Accessed on Feb. 9, 2015.
Cerner, Radiology—Streamline image management, 2 page color brochure, (fl03_332_10_v3). Downloaded from http://www.cerner.com/uploadedFiles/Clinical_Imaging.pdf. Accessed on Feb. 9, 2015.
CoActiv, EXAM-PACS, 2 page color brochure, © 2014 CoActiv, LLC. Downloaded from http://coactiv.com/wp-content/uploads/2013/08/EXAM-PACS-BROCHURE-final-web.pdf. Accessed on Feb. 9, 2015.
DR Systems, Dominator™ Guide for Reading Physicians, Release 8.2, 546 pages, (TCP-000260-A), © 1997-2009, DR Systems, Inc. Downloaded from https://resources.dominator.com/assets/004//6999.pdf. Document accessed Feb. 9, 2015.
DR Systems, DR Scheduler User Guide, Release 8.2, 410 pages, (TCP-000115-A), © 1997-2009, DR Systems, Inc. Downloaded from https://resources.dominator.com/assets/003/6850.pdf. Document accessed Feb. 9, 2015.
Fujifilm Medical Systems, SYNAPSE® Product Data, Synapse Release Version 3.2.1, Foundation Technologies, 4 page color brochure, (XBUSSY084) Aug. 2008. Downloaded from http://www.fujifilmusa.com/shared/bin/foundation.pdf. Accessed on Feb. 9, 2015.
Fujifilm Medical Systems, SYNAPSE® Product Data, Synapse Release Version 3.2.1, Server Modules and Interfaces, 4 page color brochure, (XBUSSY085) Aug. 2008. Downloaded from http://www.fujifilmusa.com/shared/bin/server-interface.pdf. Accessed on Feb. 9, 2015.
Fujifilm Medical Systems, SYNPASE® Product Data, Synapse Release Version 3.2.1, Workstation Software, 4 page color brochure, (XBUSSY082) Aug. 2008. Downloaded from http://www.fujifilmusa.com/shared/bin/workstation.pdf. Accessed on Feb. 9, 2015.
GE Healthcare, Centricity PACS, in 8 page printout. Accessed at http://www3.gehealthcare.com/en/products/categories/healthcare_it/medical_imaging_informatics_-_ris-pacs-cvis/centricity_pacs. Accessed on Feb. 9, 2015.
Handylife.com—Overview of Handy Patients Enterprise, in 2 page printout. Accessed from http://www.handylife.com/en/software/overview.html. Accessed on Feb. 18, 2015.
Handylife.com—Features of Handy Patients Enterprise, in 4 page printout. Accessed from http://www.handylife.com/en/software/features.html. Accessed on Feb. 18, 2015.
Handylife.com—Screenshots of Handy Patients Enterprise, in 2 page printout. Accessed from http://www.handylife.com/en/software/screenshots.html. Accessed on Feb. 18, 2015.
ICRco, I See the Future, in 12 pages, color brochure, (BR080809AUS), © 2009 iCRco.ClarityPACS. Downloaded from http://www.claritypacs.com/pdfs/iSeeFuture_26_Web.pdf. Accessed on Feb. 9, 2015.
Imageanalysis, dynamika, 2 page color brochure. Downloaded from http://www.imageanalysis.org.uk/what-we-do. Accessed on Feb. 9, 2015.
Imageanalysis, MRI Software, in 5 page printout. Accessed at http://www.imageanalysis.org.uk/mri-software. Accessed on Feb. 9, 2015.

(56) References Cited

OTHER PUBLICATIONS

IMSI, Integrated Modular Systems, Inc., Hosted / Cloud PACS in one page printout. Accessed at http://www.imsimed.com/#!products-services/ctnu. Accessed on Feb. 9, 2015.
Infinitt, PACS, RIS, Mammo PACS, Cardiology Suite and 3D/Advanced Visualization | Infinittna, 2 page printout. Accessed at http://www.infinittna.com/products/radiology/radiology-pacs. Accessed on Feb. 9, 2015.
Intelerad, IntelePACS, 2 page color brochure, © 2014 Intelerad Medical Systems Incoprorated. Downloaded http://www.intelerad.com/wp-content/uploads/sites/2/2014/08/IntelePACS-brochure.pdf. Accessed on Feb. 9, 2015.
Intelerad, InteleViewer, 2 page color brochure, © 2014 Intelerad Medical Systems Incoprorated. Downloaded from http://www.intelerad.com/wp-content/uploads/sites/2/2014/09/InteleViewer-brochure.pdf. Accessed on Feb. 9, 2015.
Intuitive Imaging Informatics, ImageQube, 1 page in color. Downloaded from http://www.intuitiveimaging.com/2013/pdf/ImageQube%20one-sheet.pdf. Accessed on Feb. 9, 2015.
Kuhl, Helen: Comparison Chart/PACS, Customers Are Happy, But Looking for More, (color) Imaging Techology News, itnonline.com, May 2012, pp. 24-27. Downloaded from http://www.merge.com/MergeHealthcare/media/company/In%20The%20News/merge-pacs-comparison.pdf. Accessed on Feb. 9, 2015.
LUMEDX CardioPACS 5.0 Web Viewer, Cardiopacs Module, 2 page color brochure, (506-10011 Rev A). Downloaded from http://cdn.medicexchange.com/imaging/whitepaper/cardiopacs_web_viewer.pdf?1295436926. Accessed on Feb. 9, 2015.
LUMEDX Cardiovascular Information System, CardioPACS, one page in color printout. Accessed at http://www.lumedx..com/pacs.aspx. Accessed on Feb. 9, 2015.
McKesson Enterprise Medical Imagining and PACS | McKesson, 1 page (color) printout. Accessed at http://www.mckesson.com/providers/health-systems/diaonostic-imaging/enterprise-medical-imaging. Accessed on Feb. 9, 2015.
Medweb Radiology Workflow Solutions, Radiology Workflow Solutions, Complete Workflow & Flexible Turnkey Solutions, Web RIS/PACS with Advanced Viewer, 3 page color brochure, © 2006-2014 Medweb. Downloaded from http://www.medweb.com/docs/rispacs_brochure_2014.pdf. Accessed on Feb. 9, 2015.
Merge Radiology Solutions, Merge PACS, A real-time picture archiving communication system, (PAX-21990 rev 2.0), 2 page color brochure. Downloaded from http://www.merge.com/MergeHeathcare/media/documents/brochures/Merge_PACS_web.pdf. Accessed on Feb. 9, 2015.
NOVARAD Enterprise Imaging Solutions, NOVAPACS, 2 page (color) printout. Accessed at http://ww1.novarad.net/novapacs. Accessed on Feb. 9, 2015.
PACSPLUS, PACSPLUS Server, 1 page (color) printout. Accessed at http://www.pacsplus.com/01_products/products_01.html. Accessed on Feb. 9, 2015.
PACSPLUS, PACSPLUS Workstation, 3 page (color) printout. Accessed at http://www.pacsplus.com/01_products/products_01.html. Accessed on Feb. 9, 2015.
Philips IntelliSpace PACS, in 2 color page printout. Accessed at http://www.healthcare.philips.com/main/products/healthcare_informatics/products/enterprise_imaging_informatics/isite_pacs. Accessed on Feb. 9, 2015.
Philips, IntelliSpace: Multi-modality tumor tracking application versus manual PACS methods, A time study for Response Evaluation Criteria in Solid Tumors (RECIST). 2012, Koninklijke Philips Electronics N.V., in four pages.
RamSoft, RIS PACS Teleradiology, PowerServer PACS, Lite PACS, XU PACS Compare RamSoft PACS Products, 2 color page printout. Accessed at http://www.ramsoft.com/products/powerserver-pacs-overvew. Accessed on Feb. 9, 2015.
Sage Intergy PACS | Product Summary. Enhancing Your Workflow by Delivering Web-based Diagnostic Images When and Where You Need Them, in 2 color pages. (IRV-SS-INTPACS-PSS-031309). © 2009 Sage Software Healcare, Inc. Downloaded from http://www.greenwayhealth.com/solutions/intergy/. Accessed on Feb. 9, 2015.
SclImage, Cardiology PACS, in 8 color page printout. Accessed at http://www.scimage.com/solutions/clinical-solutions/cardiology. Accessed on Feb. 9, 2015.
Sectra RIS PACS, in 2 color page printout. Accessed at https://www.sectra.com/medical/diagnostic_imaging/solutions/ris-pacs/. Accessed on Feb. 9, 2015.
Siemens syngo.plaza. Features and Benefits, in 2 color page printout. Accessed at http://www.healthcare.siemens.com/medical-imaging-it/imaging-it-radoiology-image-management-pacs/syngoplaza/features. Accessed on Feb. 9, 2015.
Simms | RIS and PACS Medical Imaging Software, in 2 color page printout. http://www.mysimms.com/ris-pacs.php. Accessed on Feb. 9, 2015.
Stryker, Imaging—OfficePACS Power Digital Imaging, in one color p. printout. Accessed from http://www.stryker.com/emea/Solutions/Imaging/OfficePACSPowerDigitalImaging/index.htm. Accessed on Feb. 9, 2015.
Stryker, OfficePACS Power—Digital Imaging, 8 page color brochure, (MPP-022 Rev 4 BC/MP300 1/07). © 2007 Stryker. Downloaded from http://www.stryker.com/emea/Solutions/Imaging/OfficePACSPowerDigitalImaging/ssLINK/emea/1557/022268. Accessed on Feb. 9, 2015.
UltraRAD—ultra VISION, 1 page (color). Downloaded from http://www.ultraradcorp.com/pdf/UltraVISION.pdf. Accessed on Feb. 9, 2015.
VioStream for VitreaView, 2 color pages printout. Accessed at http://www.vitalimages.com/solutions/universal-viewing/viostream-for-vitreaview. Accessed on Feb. 9, 2015.
Visage Imaging Visage 7, 3 color page printout. Accessed at http://www.visageimaging.com/visage-7. Accessed on Feb. 9, 2015.
Viztek Radiology PACS Software Vixtek Opal-RAD, 4 color page printout. Accessed at http://viztek.net/products/opal-rad. Accessed on Feb. 9, 2015.
Voyager Imaging—Voyager PACS Radiologist Workstation, 2 page color brochure. Downloaded from http://www.intellirad.com.au/assets/Uploads/Voyager-PacsWorkstations.pdf?. Accessed on Feb. 9, 2015.
Voyager Imaging—Voyager PACS, 3 page color brochure. Downloaded from http://www.intellirad.com.au/index.php/assets/Uploads/Voyager-Pacs3.pdf. Accessed on Feb. 9, 2015.
Non-Final Office Action from the U.S. Patent and Trademark Office for U.S. Appl. No. 15/195,208 dated Jun. 27, 2019 (7 pages).
Non-Final Office Action from the U.S. Patent and Trademark Office for U.S. Appl. No. 15/195,737 dated Jun. 27, 2019 (7 pages).
Final Office Action from the U.S. Patent and Trademark Office for U.S. Appl. No. 15/195,208 dated Aug. 3, 2020 (8 pages).
Final Office Action from the U.S. Patent and Trademark Office for U.S. Appl. No. 15/195,737 dated Aug. 19, 2020 (14 pages).
Non-Final Office Action from the U.S. Patent and Trademark Office for U.S. Appl. No. 15/195,737 dated Mar. 19, 2020 (12 pages).
Non-Final Office Action from the U.S. Patent and Trademark Office for U.S. Appl. No. 15/195,208 dated Mar. 19, 2020 (9 pages).
Applicant Initiated Interview from U.S. Patent and Trademark Office for U.S. Appl. No. 15/195,737 dated Sep. 24, 2020 (2 pages).
Pre-Brief Appeal Conference Decision from U.S. Patent and Trademark Office for U.S. Appl. No. 15/195,208 dated Oct. 30, 2020 (2 pages).

\* cited by examiner

*10140 MESA RIM ROAD*
*SAN DIEGO, CA 92121*
PHONE: *858-625-3344* Fax: *858-625-3337*

Patient Name: SAM
Patient I.D.#: 534
Referring Doctor: SACHS M.D.

Exam Date: Oct-08-10
Birth date:

Exam Time: 13:29
Age:    Sex:

320

CLICK HERE TO VIEW EXAM

CLICK HERE TO SCHEDULE EXAM ← 310

PROCEDURE: MRI OF THE BRAIN WITH AND WITHOUT INTRAVENOUS GADOLINIUM

COMPARISON: None.

INDICATIONS: Headache and nausea.

TECHNIQUE: A variety of imaging planes and parameters were utilized for visualization of suspected pathology. Images were performed without and with gadolinium contrast.

FINDINGS:
CEREBRUM:     No edema, hemorrhage, mass, acute infarction, or inappropriate atrophy.
CEREBELLUM:   No edema, hemorrhage, mass, acute infarction, or inappropriate atrophy.
BRAINSTEM:    Leftward displacement of the pons by the adjacent cerebellopontine angle tumor.
CSF SPACES:   4.5 cm right cerebellopontine angle cistern mass consistent with an acoustic neuroma.
SKULL:        No mass or other significant visible lesion.
SINUSES:      Limited views demonstrate no significant mucosal thickening or fluid.
ORBITS:       Limited views are unremarkable.
OTHER:        No abnormal meningeal or parenchymal enhancement.

CONCLUSION: Right cerebellopontine angle cistern and internal auditory canal mass, consistent with an acoustic neuroma.

Dictated and electronically authenticated by: Murray A. Reicher, M.D. on November 16-2010 at 4:13 PM
Proofread by: Murray A. Reicher, M.D. on November 17-2010 at 9:10 AM

Fig. 3

 10140 MESA RIM ROAD
SAN DIEGO, CA 92121
PHONE: 858-625-3344  Fax: 858-625-3337

Patient Name:  SAM
Patient I.D.#:  534
Referring Doctor:  SACHS M.D.

Exam Date: Oct-08-10
Birth date:

Exam Time: 13:29
Age:    Sex:

— 310

CLICK HERE TO VIEW EXAM          CLICK HERE TO SCHEDULE EXAM https://radweb.dominator.com/Scheduler2/Home/Orderfor m?PatientID= 534

PROCEDURE:   MRI OF THE BRAIN WITH AND WITHOUT INTRA

COMPARISON:  None.

INDICATIONS:  Headache and nausea.

TECHNIQUE:   A variety of imaging planes and parameters were utilized for visualization of suspected pathology. Images were performed without and with gadolinium contrast.

FINDINGS:
CEREBRUM:      No edema, hemorrhage, mass, acute infarction, or inappropriate atrophy.
CEREBELLUM:    No edema, hemorrhage, mass, acute infarction, or inappropriate atrophy.
BRAINSTEM:     Leftward displacement of the pons by the adjacent cerebellopontine angle tumor.
CSF SPACES:    4.5 cm right cerebellopontine angle cistern mass consistent with an acoustic neuroma.
SKULL:         No mass or other significant visible lesion.
SINUSES:       Limited views demonstrate no significant mucosal thickening or fluid.
ORBITS:        Limited views are unremarkable.
OTHER:         No abnormal meningeal or parenchymal enhancement.

CONCLUSION:  Right cerebellopontine angle cistern and internal auditory canal mass, consistent with an acoustic neuroma.

Dictated and electronically authenticated by: Murray A. Reicher, M.D. on November 16-2010 at 4:13 PM
Proofread by: Murray A. Reicher, M.D. on November 17-2010 at 9:10 AM

Fig. 4

|                    |                                               |                     |                  |
|--------------------|-----------------------------------------------|---------------------|------------------|

10140 MESA RIM ROAD
SAN DIEGO, CA 92121
PHONE: 858-625-3344  Fax: 858-625-3337

ON-LINE IMAGES AND RESULTS AT WWW.DOMINATOR.COM

502  Patient Name:     SMITH, JOHN              Exam Date: June 10, 2012   Exam Time: 13:55
     Patient I.D.#:    753476                   Birth date: 01/19/46       Age: 60  Sex: M
     Referring Doctor: DENNIS H. BROKER M.D.

506

504  CLICK HERE TO VIEW EXAM          CLICK HERE TO SCHEDULE EXAM

PROCEDURE: MRI OF THE BRAIN WITHOUT INTRAVENOUS GADOLINIUM

COMPARISON: None.

INDICATIONS: Headache

TECHNIQUE: A variety of imaging planes and parameters were utilized for visualization of suspected pathology.

FINDINGS:
- CEREBRUM: No edema, mass effect, hemorrhage, or inappropriate atrophy.
- CEREBELLUM: 1.2 x 1.5 x 1.0 cm mass in the right cerebellopontine angle cistern.
- BRAINSTEM: No edema, hemorrhage, or inappropriate atrophy.
- CSF SPACES: Ventricles, cisterns, and sulci are appropriate for age. No hydrocephalus or subarachnoid hemorrhage.
- SKULL: No mass or other significant visible lesion.
- SINUSES: Limited views demonstrate no significant mucosal thickening or fluid.
- ORBITS: Limited views are unremarkable.

CONCLUSION:
Right CPA mass without significant mass effect on the fourth ventricle or hydrocephalus. This mass most likely represents a meningioma or acoustic neuroma and further evaluation with a gadolinium enhanced MRI of the IACs is recommended for further evaluation.

RECOMMENDATION:
Gadolinium Enhanced MRI of the IACs. Discussed with Dr. Broker 6/10/2012 at 14:45

Dictated and electronically authenticated by: Murray A. Reicher, M.D. on 6/10/2012 at 14:50

Fig. 5A

Scheduler

| | | | |
|---|---|---|---|
| First: | John | Referring Doctor: | Dennis H. Broker, MD |
| Last: | Smith | Indication: | Right CPA mass, headache |
| Patient ID: | 753476 | Patient email: | johnsmith@direct.drphr.org |
| Birth Date: | 1/19/1946 | Patient phone: | (858) 555-5555 |
| Sex: | M | Insurance: | Aetna |

Select Procedure:

MRI BRAIN WITHOUT CONTRAST
MRI BRAIN WITH AND WITHOUT CONTRAST
MRI IACS WITH AND WITHOUT CONTRAST
MRI PITUITARY WITHOUT CONTRAST
MRI PITUITARY WITH AND WITHOUT CONTRAST

Notes about this order:

Schedule Procedure

Fig. 5B

REPORT LINKS

CROSS-REFERENCE TO RELATED APPLICATIONS

This application is a divisional of U.S. patent application Ser. No. 14/017,148, filed Sep. 3, 2013, which application claims the benefit of priority under 35 U.S.C. § 119(e) of U.S. Provisional Application No. 61/696,763, filed Sep. 4, 2012, and U.S. Provisional Application No. 61/709,626, filed Oct. 4, 2012. The disclosures of each of the foregoing applications are hereby incorporated by reference in their entireties.

BACKGROUND

Medical records, such as radiology reports that indicate results of review of medical images by a radiologist, for example, are widely used in the medical field. Because such reports are typically printed, or scanned versions of printed text documents, obtaining useful information associated with medical reports is difficult.

SUMMARY

In an embodiment, a computing system is disclosed that comprises one or more computer processors configured to execute software instructions; and one or more storage devices storing software instructions configured for execution by the one or more computer processors in order to cause the computing system to: generate a link to a scheduling system, the scheduling system configured to receive information from a viewer of a medical report in order to schedule an appointment for a patient, the link including one or more of demographic information regarding the patient embedded in the link or a patient identifier embedded in the link; embed the generated link in the medical report associated with the patient; and provide the medical report including the embedded link to a referring physician system, wherein the link is usable by the referring physician system to provide the one or more of the demographic information or the patient identifier to the scheduling system in response to selection of the link.

In another embodiment, a computing system is disclosed that comprises one or more computer processors configured to execute software instructions; and one or more storage devices storing software instructions configured for execution by the one or more computer processors in order to cause the computing system to: generate a link to a scheduling system, the scheduling system configured to receive information from a viewer of a medical report in order to schedule an appointment for a patient; embed the generated link in the medical report associated with the patient; generate a metadata pointer, the metadata pointer useable to access metadata associated with the medical report and/or the patient; and provide the medical report and metadata pointer to a referring physician system, wherein the link is usable by the referring physician system to cause the metadata pointer to be provided to the scheduling system in response to selection of the link.

In yet another embodiment, a computing system is disclosed that comprises one or more computer processors configured to execute software instructions; and one or more storage devices storing software instructions configured for execution by the one or more computer processors in order to cause the computing system to: receive a medical report associated with a patient, the medical report including a link to a medical information application configured to access one or more items of medical information associated with the patient and selectively display the one or more items of medical information associated with the patient in response to input from a user of the computing system; track particular items of the one or more items of medical information that are displayed by the computing system; and transmit a notification to one or more third party systems indicating the particular items of medical information that were displayed by the computing system.

In yet another embodiment, a computing system is disclosed that comprises one or more computer processors configured to execute software instructions; and one or more storage devices storing software instructions configured for execution by the one or more computer processors in order to cause the computing system to: determine an identity of a viewer of a medical report associated with a patient; generate a link to a secondary system, the link based at least in part on the identity of the viewer and one or more items of information associated with the medical report; and embed the generated link in the medical report.

In another embodiment, a computing system is disclosed that comprises one or more computer processors configured to execute software instructions; and one or more storage devices storing software instructions configured for execution by the one or more computer processors in order to cause the computing system to: receive a medical report associated with a patient, the medical report including a link to a medical information application configured to access one or more items of medical information associated with the patient and selectively display the one or more items of medical information associated with the patient in response to input from a user of the computing system.

BRIEF DESCRIPTION OF THE DRAWINGS

FIG. 3 illustrates an example medical report including links to an exam scheduler and an exam viewer, according to an embodiment of the present disclosure.

FIG. 4 illustrates an example medical report in which an indicator is hovering over a link, according to an embodiment of the present disclosure.

FIG. 5A illustrates another example medical report including links to an exam scheduler and an exam viewer, according to an embodiment of the present disclosure.

FIG. 5B illustrates an example scheduling application, according to an embodiment of the present disclosure.

DETAILED DESCRIPTION

Figure 1A:
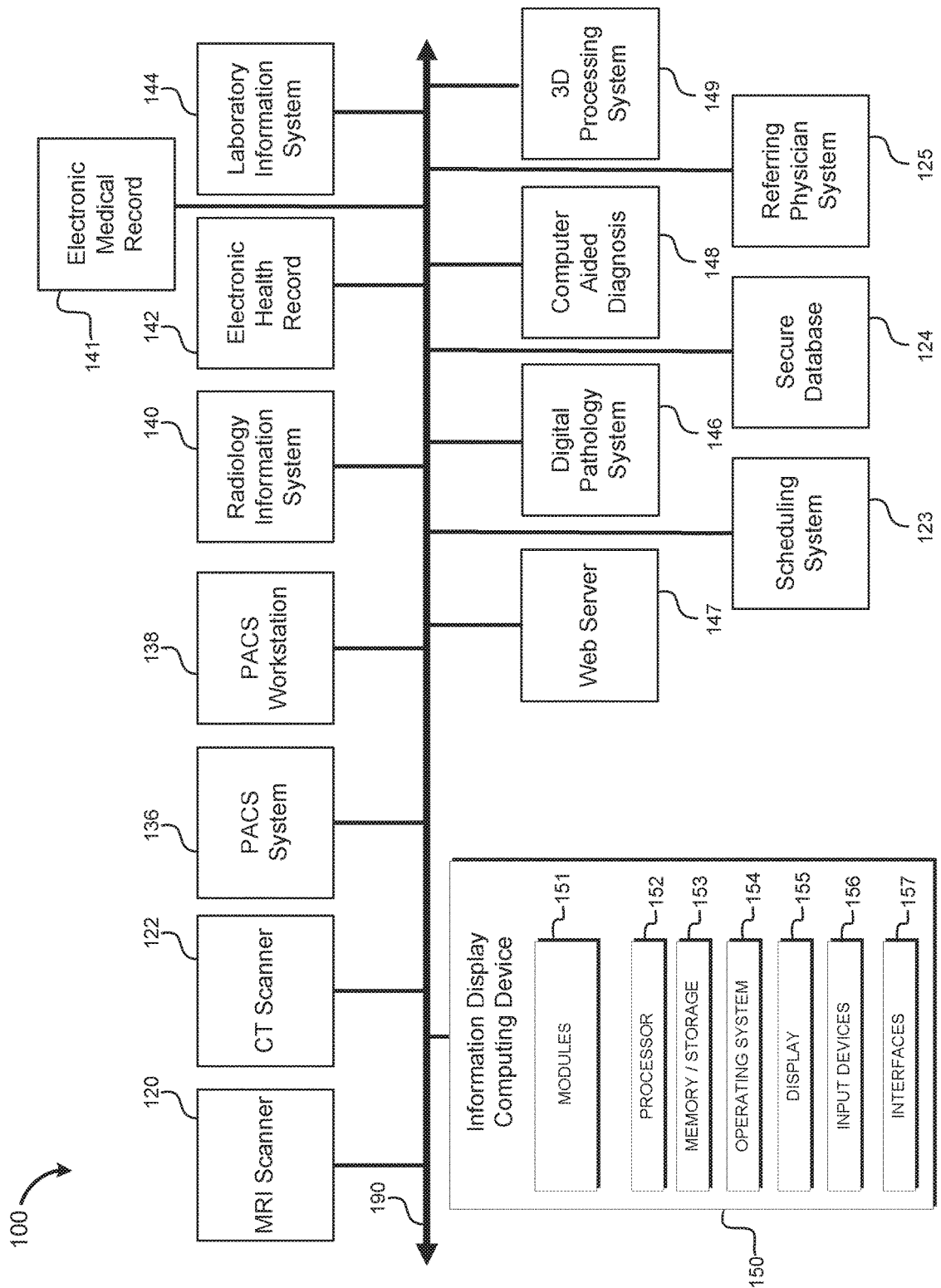
FIGS. 1A and 1B are block diagrams that show various example components of a system for displaying information, among other methods and processes, according to embodiments of the present disclosure.

Embodiments of the disclosure will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the disclosure. Furthermore, embodiments of the disclosure may include several novel features, no single one of which is solely responsible for its desirable attributes or which is essential to practicing the embodiments of the disclosure herein described.

The present disclosure describes a medical and/or clinical report that includes links to various external (and/or internal) data sources and/or systems that include information relevant to the medical report. For example, in an embodiment, a medical report may be in a PDF format (or any other format) and include links to images associated with the exam, information regarding the patient, a scheduling application useful to schedule additional procedures for the patient, and/or any other information associated with the patient or exam.

In an embodiment, a medical report including various links, as described herein, may be generated based on information received from external medical data systems. For example, a medical report from an external system may be updated to include various links to systems and sources of data related to the medical report, as described herein.

The use of links in medical reports, as described herein, may provide a number of benefits and advantages including: adding convenience to the review of medical data, and/or providing usefulness in satisfying meaningful use regulatory requirements (e.g., stage 2 requirements) and/or other requirements for sharing and availability of medical data, among others.

In order to facilitate an understanding of the systems and methods discussed herein, a number of terms are defined below. The terms defined below, as well as other terms used herein, should be construed to include the provided definitions, the ordinary and customary meaning of the terms, and/or any other implied meaning for the respective terms. Thus, the definitions below do not limit the meaning of these terms, but only provide exemplary definitions.

Within the present disclosure, the terms "doctor," "physician," "practitioner," and the like may be used interchangeably to refer to any medical or other professional that may be a user of the systems and methods described herein. However, the systems and methods described herein are not limited to use by physicians, but may also be used by other types of users including, for example, office personnel, insurance providers, scheduling assistants, and/or patients, among others.

Scheduler Links with Associated Patient Information

In an embodiment, a medical and/or clinical report associated with a patient may be generated. The medical report may include a link to a scheduling system. The link may include, for example, demographic and/or other information related to the patient. When the link is selected, the information related to the patient may be provided to the scheduling system and may be used, for example, to pre-fill patient information into a scheduling form. This may, for example, enable efficient and semi-automated appointment scheduling for the patient.

In an embodiment, the information associated with the patient (e.g., patient name, gender, date of birth, address, etc.) may be directly embedded in the link. In this embodiment, when the link is selected, the information embedded in the link may be directly transmitted to, and received by, the scheduling system (or other system indicated in the link). Thus, the scheduling system may pre-populate scheduling forms using the information included in the link and/or lookup additional information regarding the patient using the patient information. For example, if the patient's name and date of birth is included in the link (e.g., the link may be http://myhospitalscheduler.com/patient/sam.stevens/042368), that information (e.g. the patient's name is Sam Stevens, born Apr. 23, 1968) may be used to look up the patient in a patient database, such as to retrieve additional information regarding the patient that is useful in scheduling the exam.

In some embodiments, a patient identifier may be included and/or otherwise embedded in the link. In this example, the patient identifier may be transmitted to, and received by, the scheduling system as part of the link (e.g., the link may be http://myhospitalscheduler.com/patientid/M14122). The scheduling system may then automatically retrieve, from one or more other systems, information related to the patient based on the patient identifier (e.g., M14122). In an embodiment, the link may be usable to access information regarding the patient that is accessible by the scheduling system in response to the scheduling system receiving the demographic information and/or the patient identifier in the link.

FIG. 3 illustrates an example medical report, according to an embodiment, including a link 310 to an exam scheduler website or application, as well as a link 320 to view items associated with the exam, such as medical images.

FIG. 4 illustrates the same example medical report as that illustrated in FIG. 3, with the mouse (or other selector) hovering over the link 310 so that details of the link are illustrated. In this embodiment, the link 310 is configured to open a webpage that is associated with a scheduling application. In this example, the link includes a patient identifier (e.g., PatientID=534) that is usable by the scheduling application to select and/or access information associated with the specific patient identified by the patient identifier. For example, demographic information associated with the patient may be automatically selected and/or accessed from a patient database. For example, the scheduler may use the patient ID to directly retrieve information (e.g., automatically, without intervention from the individual that selects the scheduling link 310) from a patient database (e.g., either local or remotely accessible database) that is useful in scheduling an exam, such as the patient's name, birthdate, gender, scheduling preferences, etc. Accordingly, the user that is viewing the medical report and selecting the link does not need to locate the appropriate patient before continuing with the scheduling operation, such as by entering demographic information of the patient in order to locate the patient in a database of patients or creating a new record for the patient.

FIG. 5A illustrates another example medical report including patient information 502, a link 504 to view items associated with the exam (such as medical images), and a link 506 to an exam scheduler website or application. As with FIGS. 3 and 4 above, the link 504 may be selected by a user to open a viewer or other application useable for viewing information associated with the exam. For example, in response to selecting the link 504, medical images associated with the exam may be provided to the user, as shown in reference to computing device 295 of FIG. 2. The link 506 may be selected by a user to open a webpage, application, or window that is associated with the scheduling application. The link 506 may include various items of information associated with the patient that are useable by the scheduling application to identify the patient and/or schedule an appointment or exam for the patient. In the example of FIG. 5A, the link may include a patient name (e.g., John Smith), a patient identifier (e.g., 753476), referring doctor information, exam information, and/or procedure information. As described above, the various items of information may be useable to access additional information associated with the patient. In an alternative, only particular items of patient information (such as a patient ID) may be included in the link. The particular items of patient information may then be useable, as described above, to access additional information associated with the patient from, for example, a patient database. In an embodiment, the scheduling application, such as that illustrated in FIG. 5B, may be displayed in response to selecting the scheduling link 506.

As shown in the example of FIG. 5B, information regarding the patient that is the subject of the medical report of FIG. 5A is already populated in the scheduler application. The patient-related information includes, for example, a patient name (e.g., John Smith), ID (e.g., 753476), date of birth (e.g., Jan. 19, 1946), and/or sex (e.g., M), a referring physician (e.g., Dennis H. Broker, MD), a patient history, and/or a recommended exam or procedure. The information is automatically populated in the scheduler application when the link 506 is selected. This functionality may provide the scheduler and/or referrer tremendous convenience. For example, the functionality removes the need for the scheduler/referrer to look up the patient in the scheduling system. Additionally, the functionality prevents the creation of a duplicate patient record. Because the patient is accurately identified, the scheduler/referrer may access information about the patient accessible via the scheduling system. For example, the scheduler/referrer may access a record of prior exams and/or other health information directly from the scheduler application. Such information may not be available to a referring doctor outside of the link to the scheduling system.

Depending on the embodiment, scheduler links, such as links 310 and/or 506, may include an identifier of the patient (e.g., the patient ID's illustrated in FIGS. 4 and 5A) and/or specific demographic or other information associated with the patient. For example, a scheduler link used in a medical report may include name and address information (and/or any other combination of patient information) of a patient. The schedule link may be in any suitable format including, for example, https://www.patientscheduler.com/smith?harry?123?main?84321 or https://www.patientscheduler.com/?last=smith?first=john?address=123?address2=main?zip=84321.

Thus, in one embodiment, the demographic or other information associated with the patient included in the link may be used directly in pre-filling a form in the scheduling system for scheduling an appointment or exam for the patient. For example, the patient's name, address, phone number, and other necessary identifying characteristics or information may be included and/or embedded directly in the link. In another embodiment, and as described above, the demographic or other information associated with the patient included in the link may be used by the scheduling system to identify the patient and retrieve additional information related to the patient necessary for scheduling the exam or appointment. In some embodiments, both a patient ID and patient demographic information may be included in a link.

In some embodiments, the scheduler link may be configured to select a specific exam type or procedure within the scheduling application, which makes the scheduling task even easier and reduces the risk of scheduling the wrong exam. For example, the link to the scheduler application may include embedded information regarding an exam type that is recommended in the report (e.g., by the reviewing radiologist). Thus, when a referring doctor, for example, selects the scheduler link, the system may automatically activate the scheduling system, pre-populate patient information, and also pre-select the precise exam type that was recommended in the report. For example, with reference to FIG. 5B, the procedure recommended in the report may be automatically selected (in the "Select Procedure" portion of the interface) in response to the referring doctor (or other user) selecting a scheduling link with the recommended exam or procedure information encoded in the link. Thus, when the user first opens the scheduler application using the scheduler link, the appropriate exam or procedure may already be selected. In an embodiment, exam notes may be included in the scheduling application. These notes may be automatically filled when the user selects the scheduler link, or they may be added by the user after the link is selected.

Depending on the embodiment, the encoded exam type may be a code that is non-descriptive of the associated procedure (e.g., "123" or "proc1d" may be included in the schedule link and associated with a "CT Abdomen W" procedure) or the encoded exam type may provide some indication of the associated procedure (e.g., "CT-Ab-W" may be associated with a "CT Abdomen W" procedure). In other embodiments, exam or procedure types may be encoded in any other way.

In some embodiments, scheduler links may be directed to a standalone application, rather than a web application. In one embodiment, scheduler links may refer to a mobile application, such that a report viewed on a tablet device, for example, may refer to a mobile scheduling application that is used to schedule additional procedures for the patient. In one embodiment, the medical report may include multiple scheduler links that are selectable by the viewer in order to select various scheduler applications, versions of the scheduler application for different device types, etc. For example, hovering over a scheduler link may result in a display of multiple links that are selectable by the user, such as by clicking on one of the multiple links.

As described above, in some embodiments the medical report and/or link may be accessible and/or selectable by a physician. In these embodiments, the physician may be enabled to quickly access medical information related to the patient and to schedule exams or other types of appointments for the patient. In other embodiments, the medical report and/or link may be accessible and/or selectable by other types of users, such as patients. In these embodiments, the patient may be enabled to quickly access their own medical information and to easily schedule exams or other types of appointments for themselves. Various rules may determine when a patient is able to view particular medical information, as described below. In various embodiments, physicians, patients, and/or other types of users may interact with one or more computing devices, such as computing devices 150 and/or 250 (described in FIGS. 1A and 1B below), to view medical reports, select links, and/or accomplish other aspects of the present disclosure.

Metadata

In some embodiments, a clinical and/or medical report may have information embedded in the report, such as in a header portion of the report file and/or in metadata (that is part of the report file or a separate file) that may be transmitted with the report file. For example, such metadata may include information about the patient, referring doctor, demographics, and/or recommended exam information. The metadata may be used by a scheduling system, such as various scheduling systems that operate in different manners, to simplify scheduling by automating selection of certain exam scheduling parameters in view of the data included in the metadata (as described above). The metadata file may be in any available format, such as a CSV, XML, text, or other format.

Figure 6A:
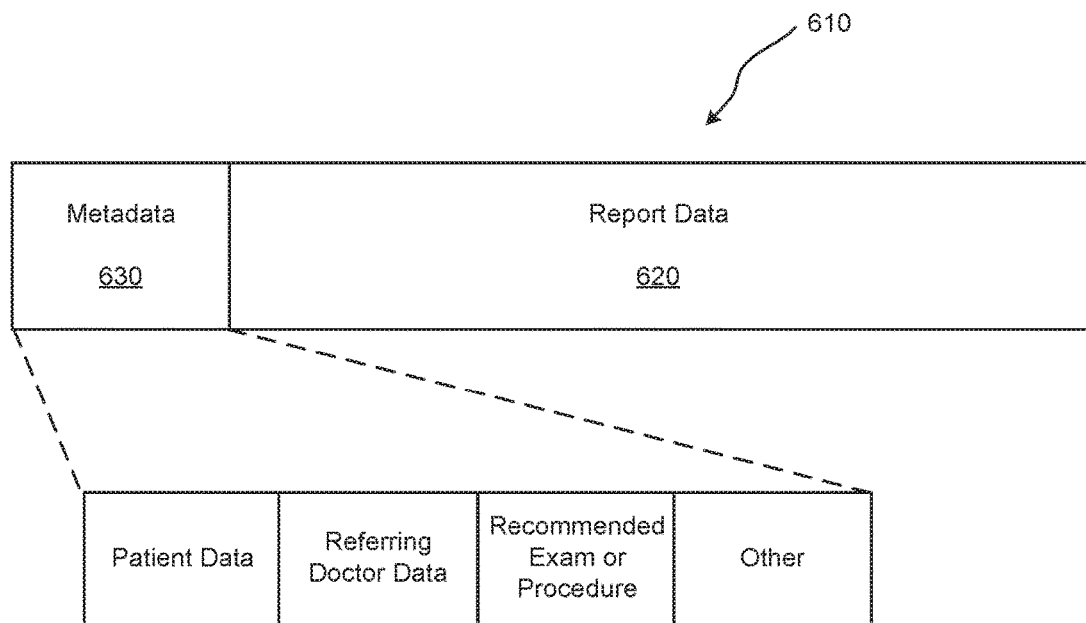
FIG. 6A illustrates a sample report file that includes both report data and metadata, according to an embodiment of the present disclosure.

FIG. 6A illustrates a sample report file 610 that includes both the report data 620 (e.g., the actual PDF data that is displayed on the referring doctor's screen), as well as metadata 630 that includes various additional information that may be useful in scheduling additional procedures for the patient. In this embodiment, the report file 610 may be a PDF, Microsoft Office file, or any other file type that includes the metadata 630 in a header (or other) portion of the report file 610. In an example, the metadata is transmitted along with the actual report data 620 so that the referring doctor, and anyone else that subsequently accesses the report file 610, also has the associated metadata.

Figure 6B:
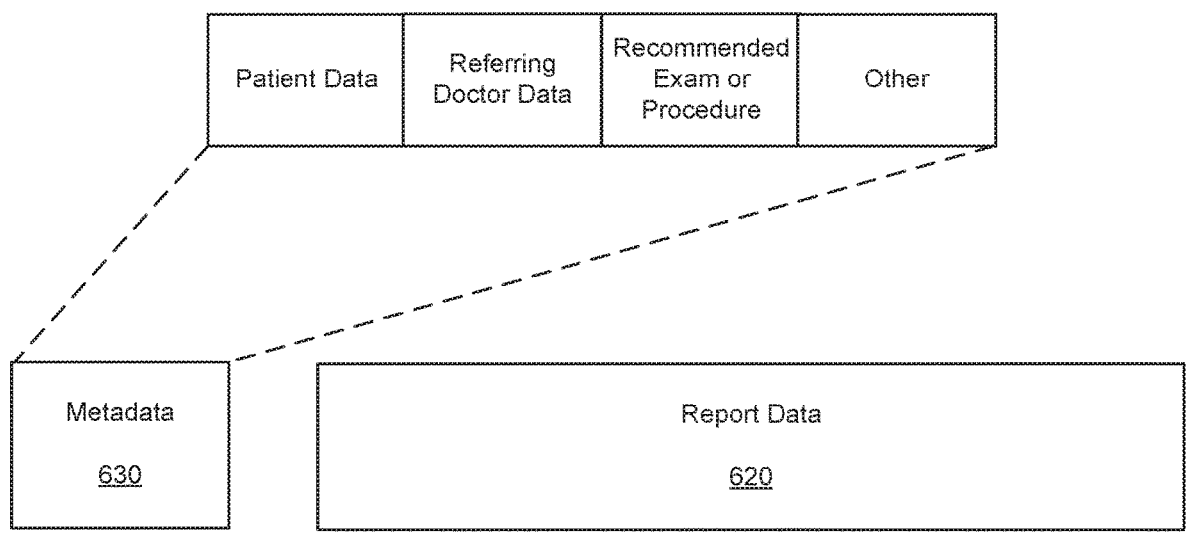
FIG. 6B illustrates a sample report including report data and metadata in separate files, according to an embodiment of the present disclosure.

In the embodiment of FIGS. 6A and 6B, the metadata 630 includes patient data, referring doctor data, recommended exam or procedure information, and/or any other information that may be relevant to exam scheduling and/or of interest to a referring doctor or other individual that accesses the report data 620. In other embodiments, other information may be stored in the metadata 630. The information in the metadata may be stored in various formats.

In the embodiment of FIG. 6B, the metadata 630 is shown as a separate file from report data 620. In this embodiment, the metadata 630 may be a file that is transmitted along with the report data 620 to the referring doctor, for example. Thus, the metadata is available for scheduling. However, the metadata 630 may be transmitted and used separate from the report data 620 because they are in separate files. In an embodiment, the metadata associated with a particular report may be stored in a separate system and/or data store that is accessible by the referring doctor, the scheduling system, and/or anyone else with access to the report file. The metadata 630 may be associated with the report data 620 by a common identifier, such as a medical report identifier that is included in the report data 620 as well as the metadata 630. Accordingly, metadata associated with any report, whether stored locally or remotely, may be located using the common identifier.

Figure 7A:
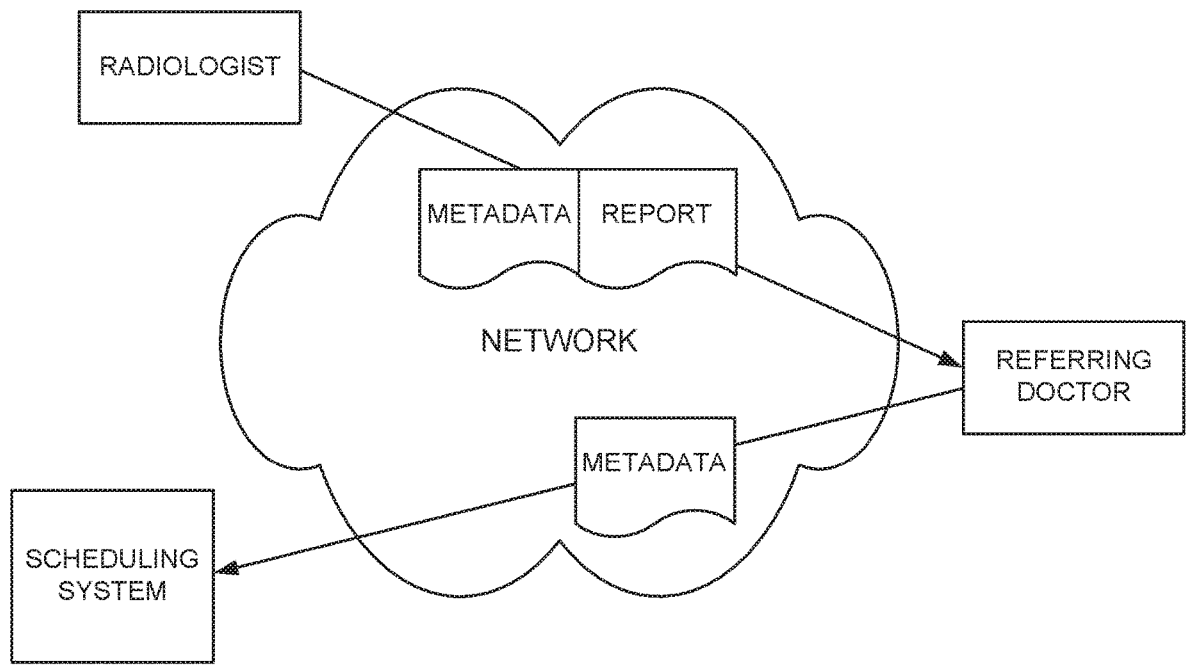
FIGS. 7A and 7B are block diagrams illustrating sample flows of information between a radiologist, referring doctor, and scheduling system, according to embodiments of the present disclosure.
Figure 7B:
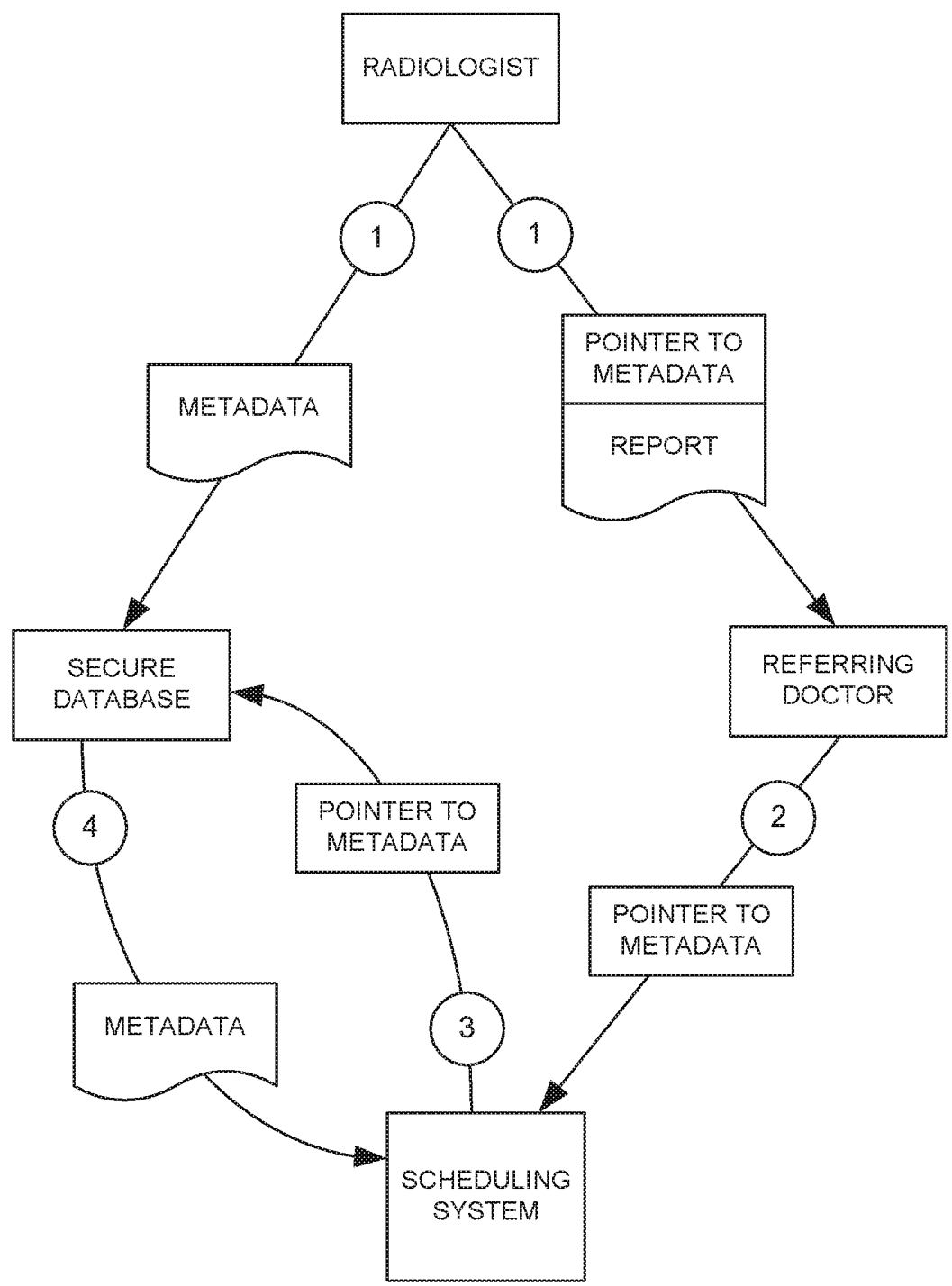

FIGS. 7A and 7B are block diagrams illustrating sample flows of information between a radiologist (or other examining doctor), a referring doctor, and a scheduling system. In other embodiments, the information may be transmitted between different entities. In an embodiment, each of the radiologist, referring doctor, and scheduling system comprise one or more computing systems that are operated by one or more human operators.

Referring now to the embodiment of FIG. 7A, a medical report is transmitted from the radiologist to the referring doctor via a network. Depending on the embodiment, the report may be transmitted immediately after completion by the radiologist or in response to a request for the report from the referring doctor. In an embodiment, the report includes metadata including information that is useful for scheduling an exam for the patient. For example, the metadata may include any of the example information discussed above with reference to FIGS. 6A and 6B and, specifically, with reference to metadata 630.

In the embodiment of FIG. 7A, the illustrated report may include the metadata in a header portion of the actual report file (e.g., similar to what is shown in FIG. 6A) or may include the metadata as a separate file (e.g., similar to what is shown in FIG. 6B). In other embodiments, the report may be transmitted separately from the metadata, possibly to different computing systems (see, for example, FIG. 7B discussed below). For example, the metadata may be sent directly to the scheduling computing system (a third party scheduling system or a schedule computer at the referring doctor's offices), while the report is sent to a report viewing computing system at the referring doctor's offices. In such an embodiment, the appropriate metadata may be accessed by the referring doctor (or scheduler) providing a medical report identifier that is received in or with the report to the scheduling system.

Turning now to FIG. 7B, an embodiment is illustrated in which the generated metadata is transmitted separately from the report. In step 1, when the report is created, the report and a pointer to associated metadata (or other identifier of the metadata) is communicated to the referring doctor system, and the metadata itself is transmitted to a secure database (or other data structure). The secure database may be, for example, any secure data store capable of storing the patient information contained in the metadata which is accessible by the scheduling system and the source (e.g., radiologist) system (for example, the secure database 124 of FIG. 1A). The metadata pointer may be any indicator capable of uniquely identifying the metadata associated with the report. The metadata pointer may be useable to retrieve the associated metadata from the secure database. In an embodiment, the metadata pointer may also include a location for the metadata or the secure database, e.g., the address of a secure, distributed or cloud-based database. In an embodiment, the metadata pointer may be associated with the report, but may contain no patient-identifying information. In an embodiment, the metadata pointer may be embedded in a link included in the report, such as a scheduling and/or viewing link. In another embodiment, the metadata pointer may be embedded in the report or stored in a separate file, similar to the way metadata storage is described in reference to FIGS. 6A and 6B.

In step 2, the user of the report, e.g., a referring doctor, may select a link in the report which opens a new application, such as a scheduling system, and the metadata pointer is transmitted to the scheduling system and/or application. In step 3, the scheduling system/application uses the metadata pointer to access the patient information stored in the secure database, such as by transmitting the metadata pointer to the secure database and/or accessing a location of the secure database indicated in the metadata pointer. In step 4, the associated metadata is accessed by the scheduling system/application. The information in the associated metadata may then be used as input to the scheduling system/application. The information may include, for example, patient demographic information, exam information, physician information, etc.

In an embodiment, the metadata pointer includes authentication information. The authentication information may be useable to authenticate the source and/or identity of the metadata pointer in order to reduce risk of unauthorized access to the secure database. In an embodiment, the secure database may be a part of the source (e.g., radiologist) system. In an embodiment, the metadata may be communicated directly from the source system to the schedule system.

In some embodiments, the metadata included with the report, or in a file separate from the report, may be used in order to schedule an exam or procedure for the patient. As shown in FIGS. 7A and 7B, the metadata (or a portion of the metadata) may be transmitted to a scheduling system for auto population/auto completion of at least a portion of the exam/procedure scheduling form. In one embodiment, the referring doctor computing system may extract information from the metadata and reformat the data for use by the scheduling system, such as a format that is used by the specific scheduling system used by the referring doctor. In one embodiment, the scheduling system is a module of the referring doctors computing system, such that the metadata may not be transmitted across a network or may be transmitted across a local area network to a computing system that is local to the referring doctor.

In the embodiments illustrated in FIGS. 7A and 7B, the metadata associated with the report advantageously allows the scheduling system, which may be any scheduling system, to receive data associated with a patient and thereby allow the scheduling system to automatically select certain parameters for scheduling of the indicated exam/procedure for the patient.

Figure 8A:
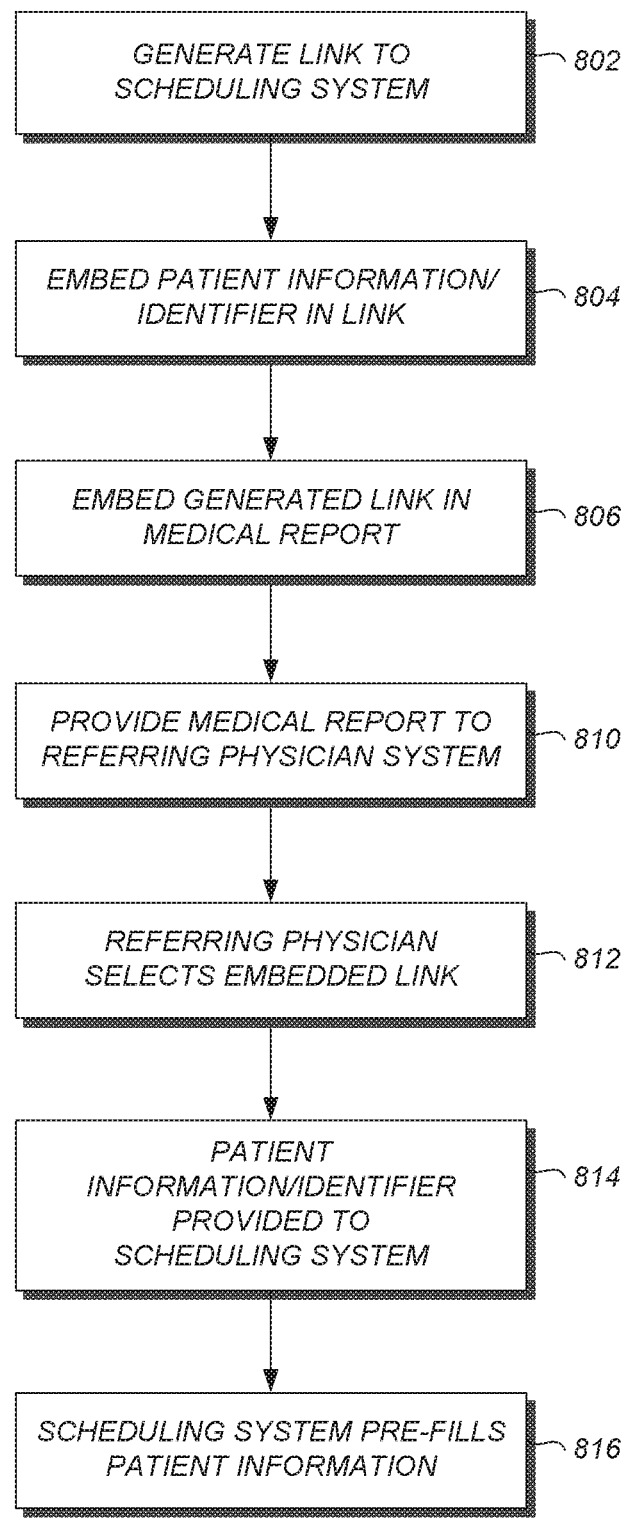
FIGS. 8A and 8B are flowcharts illustrating example processes for providing information to a scheduling system, according to embodiments of the present disclosure.
Figure 8B:
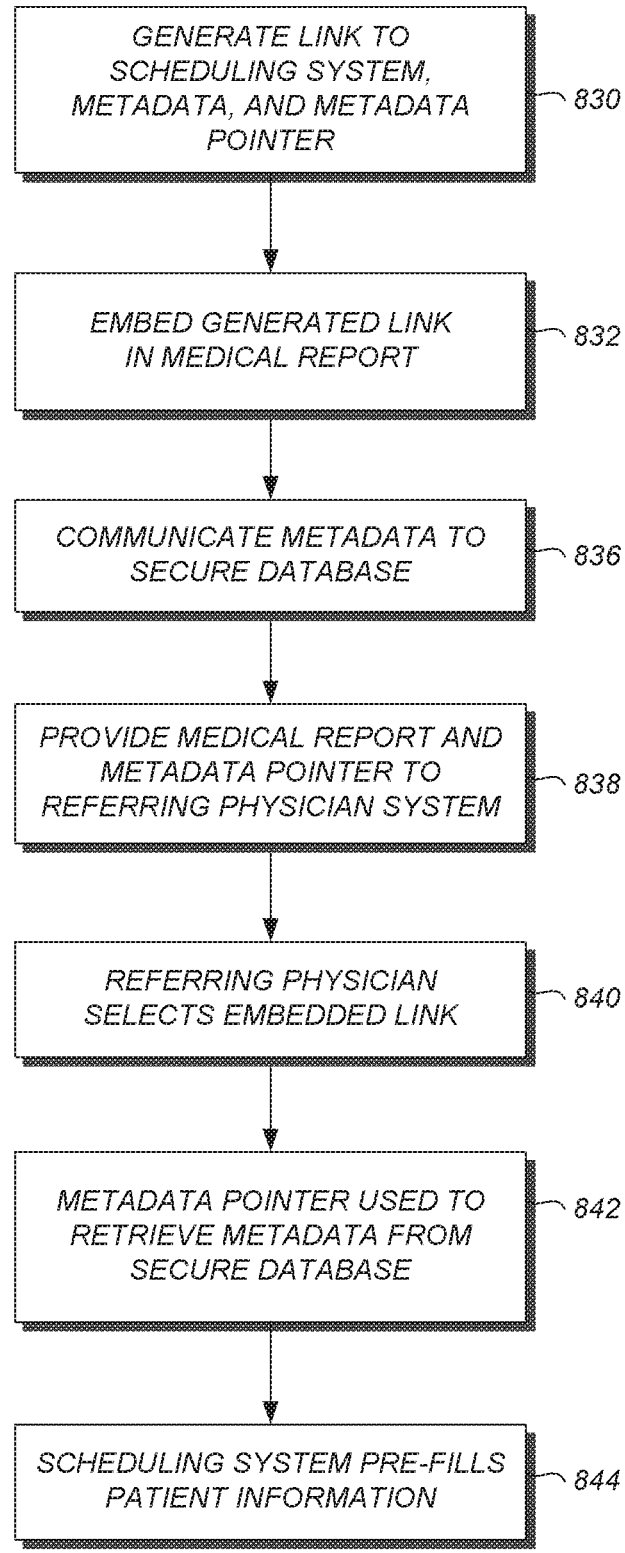

FIGS. 8A and 8B are flowcharts illustrating example processes or methods for providing the patient information to the scheduling system, according to embodiments of the present disclosure. In various embodiments, the methods described may include additional or fewer blocks and/or the blocks may be performed in a different order than is illustrated. Software code configured for execution on a computing device in order to perform the method may be provided on a tangible computer readable medium, such as a compact disc, digital video disc, flash drive, hard drive, memory device or any other tangible medium. Such software code may be stored, partially or fully, on a memory of a computing device (for example, RAM, ROM, etc.), such as the computing device 150 (see discussion of FIG. 1A below) or 250 (see discussion of FIG. 1B below), and/or other computing devices illustrated in the figures, in order to perform the respective methods.

Turning to FIG. 8A, at blocks 802 and 804, a link to the scheduling system is generated including an embedded patient identifier and/or patient demographic information, as described above in reference to FIGS. 3, 4, 5A, and 5B. At block 806, the generated link is embedded in the medical report, as further described above in reference to FIGS. 3, 4, 5A, and 5B, for example.

At block 810, the medical report, including the generated link, is provided to the referring physician system, as described above in reference to FIG. 7A, for example.

At block 812, the referring physician, or another user of the referring physician system, may select the generated link included with the medical report. In response to selection of the link, at block 814 the patient information embedded in the link is provided to the scheduling system, as described in reference to FIG. 7A above, for example. In an embodiment, the patient information embedded in the link may comprise patient metadata. As noted above, metadata associated with the patient may be embedded in the report, or may be provided in a separate file that is separately transmitted and/or made accessible to the scheduling system, as further described in reference to FIGS. 6A, 6B, 7A, and 7B, for example.

At block 816, the scheduling system may utilize the patient information provided with the link to pre-fill the scheduling form. In an embodiment, the scheduling system may utilize embedded metadata associated with the patient, or metadata provided in a separate file, to pre-fill the scheduling form. In another embodiment described above, the scheduling system may use the patient information, including patient identifying information, to access additional internal and/or external data sources of information related to the identified patient. The accessed information may then be used to pre-fill the scheduling form.

Turning now to FIG. 8B, another example process for providing the patient information to the scheduling system is shown. The process of FIG. 8B is similar to the embodiment illustrated in FIG. 7B. At block 830, a link to the scheduling system (which may or may not include embedded patient identifying information), patient metadata, and a metadata identifier are generated. At block 832, the generated link is embedded in the medical report, and at block 836, the metadata is communicated to a secure database, as described above in reference to FIG. 7B, for example. At block 838, the report and the metadata pointer are provided to the referring physician system.

At block 840, the referring physician, or another user of the referring physician system, may select the generated link included with the medical report. In response to selection of the link, at block 842 the metadata pointer is used to retrieve the associated metadata stored in the secure database, as described in reference to FIG. 7B above, for example.

At block 844, the scheduling system may utilize the patient information provided with the link and/or the retrieved metadata to pre-fill the scheduling form. In another embodiment described above, the scheduling system may use the patient information, including patient identifying information, to access additional internal and/or external data sources of information related to the identified patient. The accessed information may then be used to pre-fill the scheduling form. In an embodiment, the metadata may be retrieved directly from the source (e.g., the report generating) system.

Tracking Medical Images

In an embodiment, a method comprises generating a medical report associated with a patient, the medical report including an exam viewing link (for example, exam viewing link 320 of FIG. 3 or exam viewing link 504 of FIG. 5A) configured to allow the user to view one or more medical images of the exam (and/or other exam information) and/or selectively display medical images of the patient in response to input from a user of the computing system. Similar to the links 310 and/or 506 described above, the exam viewing links 320 and/or 504 may include one or more of a patient identifier, an exam identifier, exam type information, and/or patient demographic information. When an exam viewing link is selected, the included information may then be useable to retrieve the desired and/or associated exam images or other data.

For example, selection of the exam viewing link 504 may cause a web-based or standalone image viewing interface to open up on the user's computer, such as a user interface that is used on a Picture Archiving and Communication System (PACS) workstation. The method may further track medical images that are displayed by the computing system and/or medical images (or other medical data) that are interacted with in other ways.

In one embodiment, the method tracks which medical images the computing systems has the capability to view (e.g., which images are available on an electronic health records system of a doctor or transmitted to the doctor's computing system, even if the images are not actually displayed).

In an embodiment, the method further comprises transmitting a notification to one or more third party systems indicating the medical images that were displayed by (or otherwise made available to and/or accessed by) the computing system. In one embodiment, the one or more third party systems are identified based on meaningful use requirements and/or other regulatory requirements associated with respective third party systems. In one embodiment, the tracking criteria for each of the one or more third party systems are determined based on preferences for reporting of images displayed per ordered procedure, per patient, per system, or per eligible provider.

In one embodiment, the tracking data (e.g., data indicating which medical images were displayed by a third-party system, such as a referring doctors computing system) may be used to prove compliance with regulatory requirements, such as those originating from meaningful use regulations. For example, a particular user (e.g., a doctor) may be required to have the capability to view at least 10% of exams that are actually ordered. In this embodiment, the system that delivers the medical images, such as in response to the doctor selecting exam viewing link 504 (FIG. 5A), may also store data that is useful to prove compliance with that viewing requirement. For example, the system may store data indicating how many exams the doctor ordered and how many exams had images displayed by one or more computing devices associated with the doctor (and/or how many exams or images were made available for display to those computing devices on the doctor's Electronic Health Record (EHR) system, for example). In one embodiment, the system may provide the tracking data on a periodic basis, such as weekly or monthly, to a regulatory device so that the doctor is not required to submit any forms to complete compliance. The same or similar reporting data may be provided to the doctor and/or any other third party system.

Patient Access to Medical Data

In an embodiment, and as described above, the system can deliver or make available medical data (e.g., medical images) to a patient, such as in response to a patient selecting an image viewing link of a medical report that is provided to the patient. In one embodiment, medical data is provided to the patient only after a certain interaction with the medical data has occurred. For example, a referring doctor or radiologist may set a rule indicating that patients can receive a medical report 24 hours after the medical report is delivered to the referring doctor. Similarly, the rule may indicate that patients can receive the medical report immediately after the referring doctor provides an indication that he has reviewed the medical report. In this way, the patient is given information only after the referring doctor is prepared to discuss the information. Delivery rules based on any other criteria, or combination of criteria, may also be used to determine when medical data can be provided to patients. Additionally, different types of medical data may have different applicable rules. For example, a rule may indicate that a medical report is provided to patients after delivery to the referring doctor, but medical images may only be delivered after the patient has actually met or talked to the referring doctor. Additionally, different patients may have different applicable rules. For example, a doctor may set rules for groups of users based on the patient's age, gender, clinical indication, exam results (e.g., normal vs. abnormal), etc., such that delivery of medical data varies from patient to patient. For example, a doctor may allow immediate delivery to patients of reports that are normal or show no significant abnormality, while delaying delivery to patients of reports with abnormal results until after the doctor has indicated that the reports may be delivered (for example after the doctor has discussed the results with the patient).

Other Information and Link Enhancements

In addition to links that allow scheduling and/or exam viewing, as described above, in some embodiments a medical report may have links that allow the user to perform other functions, such as order lab tests and/or refer the patient to a specialist.

With an electronic medical information exchange, medical information such as reports, labs, and consultations from multiple sites can be automatically cross referenced. This can give a more complete picture of the patient than might be available at any individual site. For example, a doctor could be provided with links that allow him to access related information within the electronic medical information exchange (or linked EMRs or other databases). For example, when viewing a report, the doctor may want additional information to put the results of the report in the clinical context such as reports of other imaging exams (in general or related to the same body part), reports in the form of consultations from other physicians that have seen the patient, and/or lab results In an embodiment, related results may have occurred before or after the imaging exam was performed, and the links in the report may allow access to both older and newer information. For example, an internist may order lumbar spine radiographs on a patient and the reading radiologist may recommend a lumbar spine MRI based on results of the radiographs. Based on the MRI, lab tests may be ordered, for example, to evaluate for infection. The patient might then be referred to a neurosurgeon. A neurosurgeon viewing the report of the radiographs may then click on one or more links in the report that would link him to the clinical notes of the internist that led to the original exam (for example, from before the lumbar radiographs), the report of the subsequent MRI (which might have been performed at a second location and performed after the radiographs), and/or lab test results (which might have been performed at a third location and after the radiographs).

In one embodiment, reports may include a general "EMR" (Electronic Medical Records) or "EHR" (Electronic Health Record) link that would bring up links to the various EMR's and/or EHR's where the patient has medical data stored so the doctor could browse that information, assuming he has rights. Since he has rights to view the report he is viewing, there may be conditions where rights to view that report could be used to give him rights to all of some of the information in the linked EMR's and/or EHR's.

In an embodiment, the electronic medical information exchange, which may include a more complete picture of a patient's medical history than any particular individual site or EMR, may also be used to enhance ordering systems. For example, the information available in the electronic medical information exchange, possibly with linked EMR's, could also be used to prevent ordering of potentially unnecessary duplicate exams or lab tests. For example, a doctor viewing a report of a lumber spine radiograph might order a lumbar spine CT. In the scheduling systems, he could be notified by the system that the patient already had a recent lumbar spine CT based on information within, or linked to, the electronic medical information exchange.

In an embodiment, the system could be used to provide information to doctors related to a patient's radiation exposure and/or alternative exams. For example, if a doctor ordered a lumbar spine CT on a patient, he might be advised that the patient has had five abdominal CT scans in the last year and get him thinking about whether a lumbar spine MRI might answer the clinical question without additional radiation exposure.

User-Determined Links

In an embodiment, the particular links and/or types of links displayed on a particular report may vary based on one or more characteristics of the user and/or viewer. For example, the links displayed in a report may depend on permissions and/or privileges associated with the user. In these embodiments, the user may first be identified, and that identity may be authenticated, before the report (or particular links in the report) is viewable. For example, a referring doctor viewing a report may be able to see a link related to scheduling an exam, while a patient viewing the same report may be able to see a link to educational information related to a medical condition referenced in the report (but not the scheduling link).

In various embodiments, information related to user identification and/or authentication, and the associated links displayed, may be managed by the application displaying the report, e.g., an electronic health record system or personal healthcare system. In another embodiment, the identification and/or authentication information and logic related to which links are displayed may be contained within the report itself. The method of managing identification, authentication, and link viewing information may vary depending on the form the report takes, for example, users may have different rights or preferences to view links in a report based on a format of the report, such as a screen displayed by an application such as an EHR, a web page, or a self-contained document such as a PDF file.

Methods of Generating Links

In an embodiment, links displayed in a particular report may be manually chosen by a user creating the report, for example a radiologist. For example, a radiologist may want to include links to one or more informational sources, such as a cancer staging system associated with a cancer discussed in his report. The radiologist may indicate to the reporting system (or report generating system) that a link should be present in the report that links to details of the staging system referred to in the report. In another example, the user creating the report may insert a link that links to, and/or causes display of, educational material related to, or relevant to, the report. For example, the user may create a link to current medical recommendations related to breast screening exams. In general, links from the medical report to any information, systems, and/or resources (for example, the scheduling system, educational material, etc.) may be referred to as links to secondary systems.

In another embodiment, links may be automatically inserted into reports. For example, links to educational material related to a condition described in the report, characteristics of the exam performed, and/or recommendations for further workup may automatically be included in the report. In an embodiment, natural language processing may be used to detect conditions reported in the report and automatically insert associated links. For example, in the case of recommended follow-up imaging for screening, material linked to may be based on the findings within the report.

In various embodiments, when links are inserted into reports, manually or automatically, they may be manually and/or automatically set to be viewable by a subset of authorized viewers of a report. For example, a link to the scheduling system may be shown to a referring physician but not to a patient (as mentioned above).

In an embodiment, when links are automatically inserted into a report, the links inserted may be based on user preferences of various users that may be associated and/or interact with a report, e.g., the person that ordered the exam (e.g., a referring physician), the user generating the report (e.g., a radiologist), and/or the user viewing the report. For example, a referring physician that ordered the exam, and a patient viewing the report, may have different links. In another example, different referring physicians may choose different educational material to be presented to their patients via links in reports.

Messaging Via Report Links

In various embodiments, links within reports may provide messaging functionality. The messaging functionality of the links may vary, for example, based on the identity of the user or viewer of the report, and/or based on privileges or preferences of the user or viewer of the report. For example, in the context of a patient viewing a report, one or more links may enable the patient to:

Send a message to a referring doctor.
Send a message to a doctor that interpreted the exam.
Send a message to a third party to, for example, request a second opinion related to interpretation of the exam associated with the report.
Request or initiate communication of the report to an electronic health record system, e.g., a Personal Healthcare Record system utilized by the patient.

In another example, in the context of a referring doctor viewing a report, one or more links may enable the referring doctor to:

Send a message to a doctor that interpreted the exam and generated the report.
Send a message to a patient associated with the report.

In various embodiments, report links including messaging functionality may enable communications performed with secure messaging, e.g., using protocols associated with the Direct Project (www.directproject.org) and/or other secure messaging protocols. Messages using any other messaging protocols and to other entities may also be associated with report links such that messages may more easily be transmitted by a viewer of the medical report.

In an embodiment, selection of messaging links may be tracked. For example, an electronic communication of a referring physician to a patient via systems and methods described herein (for example, selection of messaging links) may be tracked. This tracked messaging data may then by analyzed in order to, for example, determine that the referring physician sent electronic messages to a particular percentage of the referring physician's patients. For example, messaging link tracking may determine that, for example, 5% of a physician's patients were contacted electronically, and/or that those patient responded. Such message tracking may be valuable to the physician (or other entity using the messaging functionality) to determine how to better communicate. Additionally, in one embodiment tracking information from multiple users (e.g., multiple physicians) may be analyzed (e.g., such as in a de-personalized manner) in order to determine messaging patterns across multiple users. For example, the tracking data may be analyzed in order to determine statistics for particular classes of physicians, for example, such as data regarding an average number of customers that receive follow-up electronic messages from pediatricians in Southern California within three days of a child's laboratory visit.

Automatic Report User Identification and/or Authentication

In an embodiment, a report user may be identified and/or authenticated automatically when a link is selected. For example, referring to FIGS. 6A and 6B user identifying information (e.g., patient data in FIGS. 6A and 6B) may be included among the metadata 630 associated with a report. The user identifying information may be associated with, for example, a referring physician who has selected a scheduling link. Referring to FIG. 7A, when a referring doctor selects a scheduling link, information identifying that particular referring physician who selected the link may be communicated to the scheduling system along with the patient information (for example, via information embedded in the link or metadata associated with the report).

In one embodiment, when a user enters a scheduling system via a scheduling link in a report, the scheduling system may identify and/or authenticate the user before the user is allowed to proceed. For example, the user may be required to provide a login and/or password. In embodiments in which user information is automatically transferred to the scheduling systems along with the patient information, the user's login and/or name may be automatically provided to the scheduling system. In an example, the user's login may automatically be filled in such that the user only has to provide their password. In another example, all authentication credentials may automatically be provided such that the user is automatically identified and authenticated by the scheduling system. In yet another example, the name of the user may be provided to the scheduling system such that the user's name may be compared against the credentials (login and password) provided by the user to ensure the identified user matches the identity of the user who selected the link.

In one example, the scheduling system may identify a user who is authorized to order an exam on behalf of a referring physician. In this embodiment, the scheduling system may automatically enter the name of the ordering physician who has authorized the user. In another example, identification and/or authentication information used to allow the physician (or other user) to view an exam may be automatically transmitted to the scheduling system (or other system) so that the physician may not have to provide credentials (e.g., login and password) to be re-authenticated. Further, the name of the automatically authenticated physician may be automatically indicated as the ordering physician for the exam to be scheduled.

Example Computing Systems

FIG. 1A is a block diagram which shows the various components of a system 100 for displaying information utilizing certain systems and methods described herein. As shown, the system 100 may include an information display computing device 150 (also referred to herein as a "computing device 150") and may include other systems, including those shown in FIG. 1A. For example, other systems may include various specialized computing systems including an MRI scanner 120, a CT Scanner 122, a PACS System 136, a PACS Workstation 138, a Radiology Information System 140, an Electronic Medical Record (EMR) System 141, an Electronic Health Record (EHR) System 142, a Laboratory Information System 144, a Digital Pathology System 146, a web server 147, a Computer Aided Diagnosis System 148, a 3D Processing System 149, a Scheduling System 123, a Secure Database 124, and a Referring Physician System 125.

The computing device 150 may take various forms. In one embodiment, the information display computing device 150 may be a computer workstation having modules 151, such as software modules that provide the functionality described above with reference to the other figures.

In one embodiment, the information display computing device 150 comprises a server, a desktop computer, a workstation, a PACS workstation, a laptop computer, a mobile computer, a smartphone, a tablet computer, a cell phone, a personal digital assistant, a gaming system, a kiosk, an audio player, any other device that utilizes a graphical user interface, including office equipment, automobiles, airplane cockpits, household appliances, automated teller machines, self-service checkouts at stores, information and other kiosks, ticketing kiosks, vending machines, industrial equipment, and/or a television, for example.

The information display computing device 150 may run an off-the-shelf operating system 154 such as a Windows, Linux, MacOS, Android, or iOS, or mobile versions of such operating systems. The information display computing device 150 may also run a more specialized operating system which may be designed for the specific tasks performed by the computing device 150, or any other available operating system.

The information display computing device 150 may include one or more computing processors 152. The computer processors 152 may include central processing units (CPUs), and may further include dedicated processors such as graphics processor chips, or other specialized processors. The processors generally are used to execute computer instructions based on the information display software modules 151 to cause the computing device to perform operations as specified by the modules 151. The modules 151 may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. For example, modules may include software code written in a programming language, such as, for example, Java, JavaScript, ActionScript, Visual Basic, HTML, C, C++, or C #. While "modules" are generally discussed herein with reference to software, any modules may alternatively be represented in hardware or firmware. Generally, the modules described herein refer to logical modules that may be combined with other modules or divided into sub-modules despite their physical organization or storage.

The information display computing device 150 may also include memory 153. The memory 153 may include volatile data storage such as RAM or SDRAM. The memory 153 may also include more permanent forms of storage such as a hard disk drive, a flash disk, flash memory, a solid state drive, or some other type of non-volatile storage.

The information display computing device 150 may also include or be interfaced to one or more display devices 155 that provide information to the users. Display devices 155 may include a video display, such as one or more high-resolution computer monitors, or a display device integrated into or attached to a laptop computer, handheld computer, smartphone, computer tablet device, or medical scanner. In other embodiments, the display device 155 may include an LCD, OLED, or other thin screen display surface, a monitor, television, projector, a display integrated into wearable glasses, or any other device that visually depicts user interfaces and data to viewers.

The information display computing device 150 may also include or be interfaced to one or more input devices 156 which receive input from users, such as a keyboard, trackball, mouse, 3D mouse, drawing tablet, joystick, game controller, touch screen (e.g., capacitive or resistive touch screen), touchpad, accelerometer, video camera and/or microphone.

The information display computing device 150 may also include one or more interfaces 157 which allow information exchange between information display computing device 150 and other computers and input/output devices using systems such as Ethernet, Wi-Fi, Bluetooth, as well as other wired and wireless data communications techniques.

The modules of the information display computing device 150 may be connected using a standard based bus system. In different embodiments, the standard based bus system could be Peripheral Component Interconnect ("PCI"), PCI Express, Accelerated Graphics Port ("AGP"), Micro channel, Small Computer System Interface ("SCSI"), Industrial Standard Architecture ("ISA") and Extended ISA ("EISA") architectures, for example. In addition, the functionality provided for in the components and modules of information display computing device 150 may be combined into fewer components and modules or further separated into additional components and modules.

The information display computing device 150 may communicate and/or interface with other systems and/or devices. In one or more embodiments, the computing device 150 may be connected to a computer network 190. The computer network 190 may take various forms. It may include a wired network or a wireless network, or it may be some combination of both. The computer network 190 may be a single computer network, or it may be a combination or collection of different networks and network protocols. For example, the computer network 190 may include one or more local area networks (LAN), wide area networks (WAN), personal area networks (PAN), cellular or data networks, and/or the Internet.

The information display computing device 150 may be configured to interface with various networked computing devices via the network 190 in order to provide efficient and useful review of data that.

Depending on the embodiment, the other devices illustrated in FIG. 1A may include some or all of the same components discussed above with reference to the Information Display Computer Device 150.

Figure 1B:
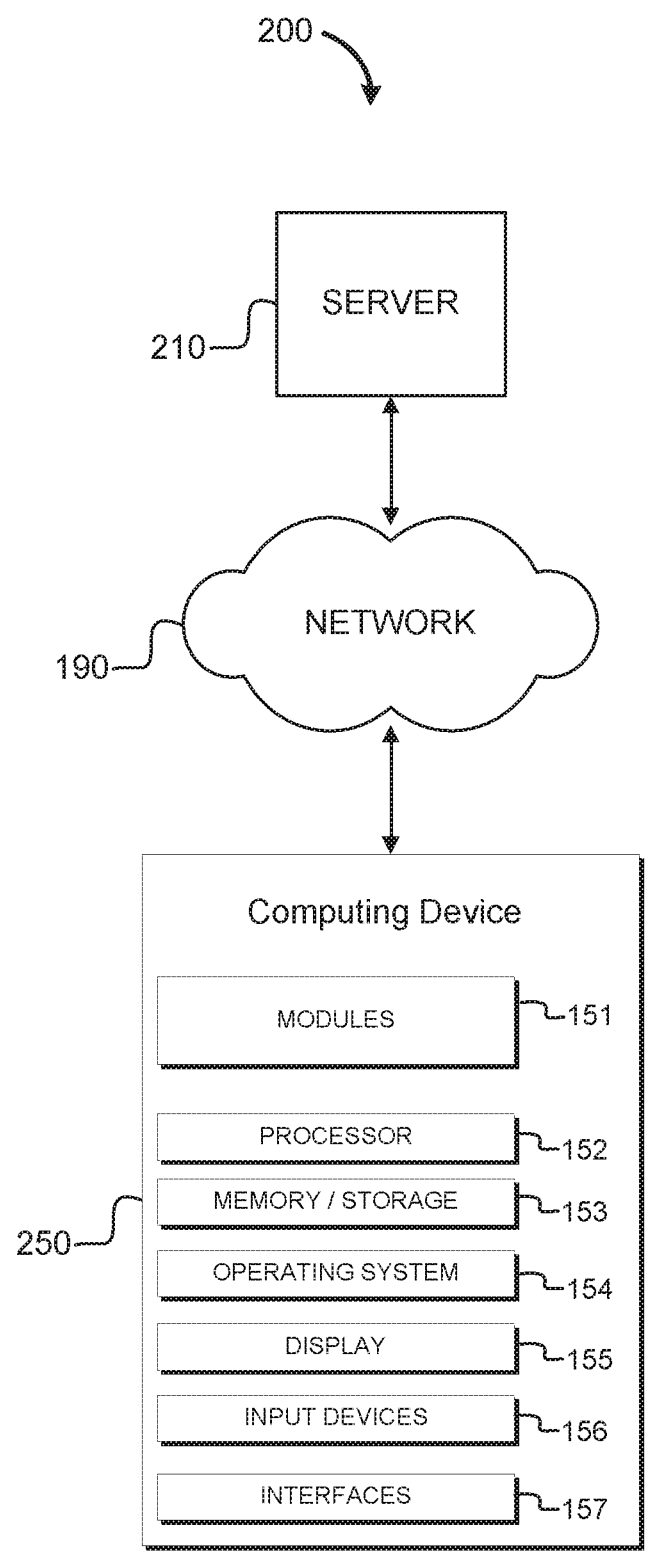

FIG. 1B is a system diagram illustrating various components of a system 200 for managing data utilizing certain systems and methods described herein. As shown, the system 200 includes a computing device 250 and may include other systems, including those shown in FIG. 2.

The computing device 250 may take various forms. In one embodiment, the computing device 250 may be a computer workstation having modules 151. In other embodiments, modules 151 may reside on another computing device, such as a web server, and the user directly interacts with a second computing device that is connected to the web server via a computer network. As mentioned above, the modules 151 may be configured to cause the computing device to perform operations implementing the functionality of the systems and methods described herein and in reference to the other figures above.

In one embodiment, the computing device 250 comprises a server, a desktop computer, a workstation, a laptop computer, a mobile computer, a Smartphone, a tablet computer, a cell phone, a personal digital assistant, a gaming system, a kiosk, an audio player, any other device that utilizes a graphical user interface, including office equipment, automobiles, airplane cockpits, household appliances, automated teller machines, self-service checkouts at stores, information and other kiosks, ticketing kiosks, vending machines, industrial equipment, and/or a television, for example.

The computing device 250 may run an off-the-shelf operating system 154 such as a Windows, Linux, MacOS, Android, or iOS. The computing device 250 may also run a more specialized operating system which may be designed for the specific tasks performed by the computing device 250.

As with computing device 150 described herein with reference to FIG. 1A, computing device 250 may include one more computing processors 152, may include memory storage 153, may include or be interfaced to one more display devices 155, may include or be interfaced to one or more input devices 156, and/or may include one or more interfaces 157.

Computing device 250 may communicate and/or interface with other systems and/or devices via network 190, as described herein with reference to FIG. 1A.

Also connected to network 190 may be a server 210 that communicates with computing device 250, for example allowing communication of images or other data (e.g., medical or non-medical data, such as e-commerce data) between server 210 and computing device 250.

Figure 2:
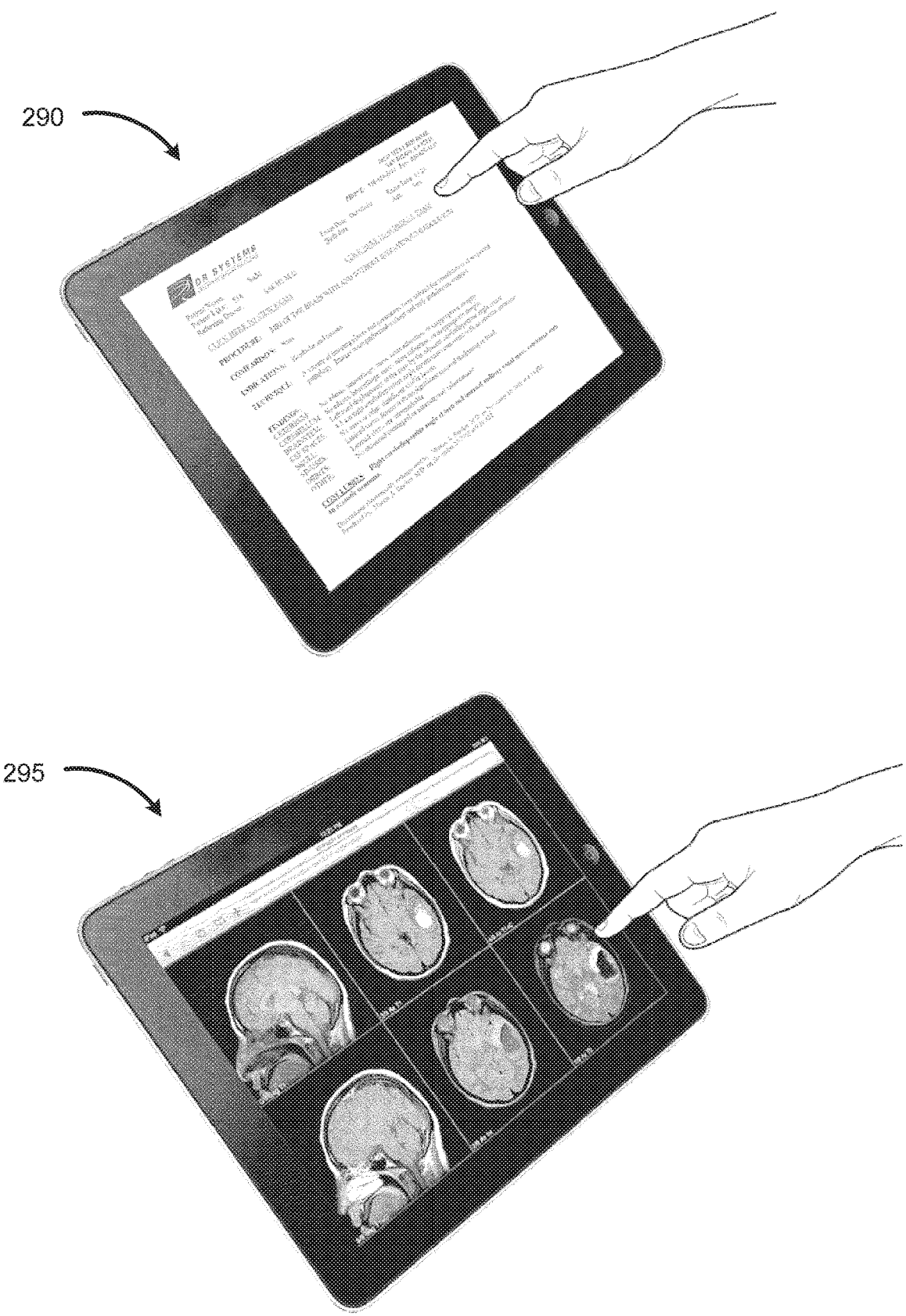
FIG. 2 illustrates two mobile information display computing devices, according to embodiments of the present disclosure.

FIG. 2 illustrates two mobile information display computing devices. In particular, FIG. 2 illustrates a tablet computing device 290 and a tablet computing device 295 that may execute a mobile operating system such as iOS, Android, or Windows Mobile, or that may execute desktop computer operating systems, such as those discussed above with reference to the computing device 150. For example, FIG. 2 shows an example of a user interacting with the tablet computing device 290 on which is displayed a medical report (including links), as described above. Additionally, FIG. 2 shows an example of the user interacting with the tablet computing device 295 on which are displayed medical images. In the examples, the tablet computing device 290 and the tablet computing device 295 may be the same device, and the user may have been linked to the images by selecting a link included in the medical report. Any references herein to the Information Display Computer Device 150, or more generally to a Computer Device or simply a computing device, computing system, or computer, may refer to one of any suitable computing device including some or all of the components of computing devices 150 or 250. The devices of FIG. 2 utilize touch screen input, but other input devices could be utilized on these devices, as well as other devices, including a computer mouse, keyboard, trackball, etc.

In various embodiments, various components of the devices and systems described above with reference to FIGS. 1A, 1B, and 2, may be used to implement the systems and methods described in the present disclosure. In an embodiment, the medical report may be generated by a device such as the computing device 150 (the computing device 150 being in communication with various other systems and data sources). In an embodiment, the medical report may be transmitted over a network, for example, from one computing device to another, as shown in FIGS. 1A, 1B, and 7. For example, one or more of the server 210 and the computing device 250 may be used to implement a system operated by the radiologist and/or the referring doctor (of FIG. 7), and/or the scheduling system (as shown in FIG. 7). Information and data may thereby be transmitted, received, and/or processed by the various components of the systems and methods described above. In an embodiment, the referring doctor of FIG. 7 interacts with a system that may be referred to as a referring doctor system or a referring physician system. In an embodiment, as described above, the system may be used by a patient that is accessing medical data and/or scheduling an appointment.

Other

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be embodied in, and partially or fully automated via, software code modules executed by one or more general purpose computers. For example, the methods described herein may be performed by an Information Display Computing Device and/or any other suitable computing device. The methods may be executed on the computing devices in response to execution of software instructions or other executable code read from a tangible computer readable medium. A tangible computer readable medium is a data storage device that can store data that is readable by a computer system. Examples of computer readable mediums include read-only memory, random-access memory, other volatile or non-volatile memory devices, CD-ROMs, magnetic tape, flash drives, and optical data storage devices.

Many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the disclosed systems and methods can be practiced in many ways. As is also stated above, the use of particular terminology when describing certain features or aspects should not be taken to imply that the terminology is being re-defined herein to be restricted to including any specific characteristics of the features or aspects of disclosed systems and methods with which that terminology is associated.

What is claimed is:

1. A computing system comprising:
   one or more computer processors configured to execute software instructions; and
   one or more storage devices storing software instructions configured for execution by the one or more computer processors in order to cause the computing system to:
   receive a medical report associated with a patient, the medical report including a link to a medical information application configured to access one or more items of medical information associated with the patient and selectively display the one or more items of medical information associated with the patient in response to input from a user of the computing system;
   track access activity of particular items of the one or more items of medical information that are displayed by the computing system, wherein the particular items of the one or more items of medical information are accessed by the computing device via one or more servers over one or more networks;
   determine tracking criteria for each of one or more third party systems based on preferences of each of the one or more third party systems, the tracking criteria for each of the one or more third party system specifying whether reporting of items displayed is to be reported to the third party system per ordered procedure, per patient, per system, or per eligible provider; and
   automatically transmit a notification to each of the one or more third party systems indicating the particular items of medical information that were displayed by the computing system based on the tracking criteria for each of the one or more third party systems.

2. The computing system of claim 1, wherein the items of medical information comprise medical images, and wherein the medical information application comprises an image viewing application configured to access one or more medical images of the patient and selectively display the one or more medical images in response to input from the user.

3. The computing system of claim 1, wherein the one or more third party systems are identified based on meaningful use requirements and/or other regulatory requirements associated with respective third party systems.

4. The computing system of claim 1, wherein the instructions are further configured to cause the computing system to:
   access one or more access criteria indicating when the items of medical information may be displayed to the patient;
   in response to input from the patient requesting access to an item of medical information, determine, based on the one or more access criteria, whether the item of medical information may be displayed to the patient; and
   in response to determining that the item of medical information may be displayed to the patient, display the item of medical information to the patient.

5. The computing system of claim 4, wherein the one or more access criteria indicate that a particular item of medical data may not be displayed to the patient until after the particular item has been transmitted to a referring physician and/or displayed to a referring physician.

6. The computing system of claim 4, wherein the one or more access criteria indicate that a particular item of medical data may not be displayed to the patient until after the medical report has been displayed to a referring physician.

7. The computing system of claim 4, wherein the one or more access criteria are based on types and/or classes of medical information.

8. The computing system of claim 4, wherein the one or more access criteria are based on characteristics of the patient.

9. The computing system of claim 8, wherein the characteristics of the patient include at least one of age, gender, clinical indication, or an associated exam result.

10. A computer-implemented method comprising:
by one or more computer processors executing software instructions:
receiving a medical report associated with a patient, the medical report including a link to a medical information application configured to access one or more items of medical information associated with the patient and selectively display the one or more items of medical information associated with the patient in response to input from a user of the computing system;
tracking the access activity of particular items of the one or more items of medical information that are displayed by the computing system, wherein the particular items of the one or more items of medical information are accessed by the computing system via one or more servers over one or more networks;
determining tracking criteria for each of one or more third party systems based on preferences of each of the one or more third party systems, the tracking criteria for each of the one or more third party systems specifying whether reporting of items displayed is to be reported to the third party system per ordered procedure, per patient, per system, or per eligible provider; and
automatically transmitting a notification to each of the one or more third party systems indicating the particular items of medical information that were displayed by the computing system based on the tracking criteria determined for each of the one or more third party systems.

11. The computer-implemented method of claim 10, wherein the items of medical information comprise medical images, and wherein the medical information application comprises an image viewing application configured to access one or more medical images of the patient and selectively display the one or more medical images in response to input from the user.

12. The computer-implemented method of claim 10, wherein the one or more third party systems are identified based on meaningful use requirements and/or other regulatory requirements associated with respective third party systems.

13. The computer-implemented method of claim 10 further comprising:
by one or more computer processors executing software instructions:
accessing one or more access criteria indicating when the items of medical information may be displayed to the patient;
in response to input from the patient requesting access to an item of medical information, determining, based on the one or more access criteria, whether the item of medical information may be displayed to the patient; and
in response to determining that the item of medical information may be displayed to the patient, displaying the item of medical information to the patient.

14. The computer-implemented method of claim 13, wherein the one or more access criteria indicate that a particular item of medical data may not be displayed to the patient until after the particular item has been transmitted to a referring physician and/or displayed to a referring physician.

15. The computer-implemented method of claim 13, wherein the one or more access criteria indicate that a particular item of medical data may not be displayed to the patient until after the medical report has been displayed to a referring physician.

16. The computer-implemented method of claim 13, wherein the one or more access criteria are based on types and/or classes of medical information.

17. The computer-implemented method of claim 13, wherein the one or more access criteria are based on characteristics of the patient.

18. A non-transitory computer readable storage medium having software instructions embodied therewith, the software instructions executable by one or more processors to cause the one or more processors to:
receive a medical report associated with a patient, the medical report including a link to a medical information application configured to access one or more items of medical information associated with the patient and selectively display the one or more items of medical information associated with the patient in response to input from a user of the computing system;
track the access activity of particular items of the one or more items of medical information that are displayed by the computing system, wherein the particular items of the one or more items of medical information are accessed by the computing system via one or more servers over one or more networks;
determine tracking criteria for each of one or more third party systems based on preferences of each of the one or more third party systems, the tracking criteria for each of the one or more third party systems specifying, whether reporting of items displayed is to be reported to the third party system per ordered procedure, per patient, per system, or per eligible provider; and
automatically transmit a notification to each of the one or more third party systems indicating the particular items of medical information that were displayed by the computing system based on the tracking criteria for each of the one or more third party systems.

* * * * *